United States Patent [19]

Birch

[11] 4,038,139
[45] July 26, 1977

[54] CELL CULTURE MEDIUM
[75] Inventor: John R. Birch, High Wycombe, England
[73] Assignee: G. D. Searle & Co., Limited, High Wycombe, England
[21] Appl. No.: 705,862
[22] Filed: July 16, 1976
[51] Int. Cl.² .............................................. C12B 3/00
[52] U.S. Cl. .................................................... 195/1.8
[58] Field of Search ......................................... 195/1.8
[56] References Cited
U.S. PATENT DOCUMENTS
3,910,819 10/1975 Rembaum et al. ..................... 195/1.8

Primary Examiner—Sam Rosen
Attorney, Agent, or Firm—John J. McDonnell

[57] ABSTRACT

The present invention relates to culture media in which animal cells may be grown and more particularly to such culture media containing animal serum and methods for culturing cells in the media. Specifically, the present invention encompasses a culture medium for lymphoblast cells comprising an aqueous nutrient medium containing 0.5% – 20% swine serum and about 0.1% of a surfactant which inhibits the precipitation of proteins and methods for using said medium.

5 Claims, No Drawings

CELL CULTURE MEDIUM

The present invention relates to culture media in which animal cells may be grown and more particularly to such culture media containing animal serum and methods for culturing cells in the media. Specifically, the present invention encompasses a culture medium for lymphoblast cells comprising an aqueous nutrient medium containing 0.5% − 20% swine serum and about 0.1% of a surfactant which inhiibits the precipatation of protein and methods for using said medium.

A culture medium containing swine serum in combination with 0.05 − 5% polyoxyethylene-polyoxypropylene copolymer or methyl cellulose as surfactants to inhibit protein precipitation is particularly preferred.

The present invention thus involves improved methods for culturing lymphocyte cells in an aqueous nutrient medium containing animal serum wherein the improvement comprises using 0.5% − 20% swine serum in combination with a small amount of surfactant to prevent precipitation of serum protein — about 0.05 − 5% methyl cellulose or polyoxyethylene-polyoxypropylene copolymer coplymer are preferred surfactants.

It is well known that animal cells may be grown in liquid culture medium, *Tissue Culture*, Kruse et al. Academic Press, N.Y., N.Y. 1973. Such media contain many independent factors which are found by experimentation to promote the maximum growth of the cultured cells. The cells grown in culture are used for many different purposes, for example the production of interferon-like materials, enzymes or other cell products, including antigens.

One particular component of certain culture media is animal serum. This appears to be necessary for the continued rapid growth of many cells. In many circumstances the serum which is most effective in allowing maximum cell populations to be achieved is foetal calf or newborn calf serum since this serum lacks antibodies which inhibit cell growth. However, this serum is extremely expensive and its high cost prevents the ecomonic growth of cells in media containing this serum.

It has now been found that in the culture of lymphoid cell lines, calf serum supports growth only very poorly and that foetal calf serum is required to achieve high cell yields.

It has now surprisingly been found that swine serum will not only support the growth of lymphoid cells but gives yields superior to those obtained using foetal calf serum. Since swine serum is very considerably cheaper than foetal calf serum this discovery reduces the cost of growing those cells which require such sera.

This discovery is surprising because it is generally accepted that swine serum will not support the growth of most types of cells because of the expectation of cell growth inhibiting antibodies.

The present invention therefore provides novel artificial media, for growing animal cells in culture, containing swine serum as part or all of the serum component. A further aspect of the present invention provides a method of growing animal cells in culture comprising inoculating an artificial culture medium containing swine serum with viable animal cells, allowing the cells to grow in culture and harvesting the cells or the medium in which they are grown.

The effectiveness of swine serum in the process of the invention is illustrated in the following table which compares the results obtained in the growth of human lymphoblasts (MICH) using various sera.

TABLE I

| Serum (10% v/v) | Minimum Population Doubling Time (h) | Maximum Population/ ml × $10^5$ (inoculum deducted) |
| --- | --- | --- |
| Foetal Calf | 19 − 26 | 10 − 13 |
| Swine | 16 − 25 | 11 − 13 |
| Lamb | 68 | 4 |
| Horse | 18 | 11 |
| Chicken | — | 0 |
| Newborn Calf | 34 | 7.7 |

(With horse serum there is batch to batch variation with cell lines other than MICH).

Numerous different lymphoid cell lines may be grown in the present culture media and the method of growing cells according to the second aspect of the present invention is not restricted to any particular cell line. Lymphoblasts for example, MICH, ODLA, $BR_17$, $BR_18$, BEC 11, RPM 1788, $RAJ_1$, and NAMALVA are commonly available cell lines which are grown according to procedures set out in Examples 1 − 4, are one kind of cell which is widely grown in suspension culture, where the cells are suspended in a liquid medium which is greatly agitated. The cell population increases and reaches a maximum level, at which stage the cells are harvested and a sample diluted to establish a further culture. Alternatively, the medium may be separated from the cells and material which may have been released into the medium is separated and collected. By this means, interferon or interferon-like materials, lymphokines and released membrane antigens may be collected from culture media.

A liquid medium for the growth of cells such as lymphoblasts, contains many components additional to the serum, for example, amino acid or protein nutrients, vitamins and metabolic substrates. To such mixtures are added requisite sera at concentrations which are selected by experimentation to allow the maximum rate of cell growth and cell population. Typically, serum constitutes between 0.5% and 20% (5% and 20% preferably) of the total medium.

Surfactants which retain protein in solution during cell growth are suitable for practicing the present invention. Blockpolymer surfactants prepared by adding ethylene oxide to both ends of a polyoxypropylene polymer and sold under the tradename Pluronic F68 by Wyandotte Chemical Co. are particularly useful. These polymers have a molecular weight of about 8750 and 80% of the molecular weights consists of hydrophilic polyoxyethylene groups and the remainder of hydrophobic polyoxypropyl groups. Methyl cellulose is a preferred surfactant for preventing the precipitation of protein. Generally concentrations of at least the critical micelle concentration of the surfactant are required and about 0.05% − 5% is the preferred amount.

The swine serum used for the present invention is prepared by conventional techniques and is commerically available. It can be used as a complete replacement for alternative sera or as a partial replacement in which it forms a major production of the total serum. It may be preferred to include some foetal calf serum or other serum, where this is shown to have advantageous properties for the particular cells concerned.

The invention will be further described by reference to the following examples.

EXAMPLE 1

Human lymphoblast cells may be grown through successive subcultures using a conventional cell culture medium in which the serum component consists of swine serum.

A MICH strain of cultured human lymphoblast cells were grown in shake-flast culture through successive subcultures. The culture medium was conventional medium to which had been added the sera as specified. The growth rates through successive cultures in the presence of 10% swine serum, 5% foetal calf serum and 5% newborn calf serum and 10% newborn calf serum. High growth rates of approximately the same order of magnitude and maximum cell population densities are achieved using swine serum, in comparison with the expensive foetal and newborn calf sera. The swine serum produces generally higher growth rates and cell population densities.

EXAMPLE 2

Human cells may be grown in large scale culture vessels using a medium in which the serum component consists of swine serum. OLDA strain human lymphocyte cells are grown in a 30 liter fermenter using a conventional basic medium to which is added 10% swine serum. A small amount of surfactant, about 1 mg/ml, (for example, polyoxyethylene-polyoxypropylene copolymer sold as Pluronic F68 or methyl cellulose) is also added to prevent precipitation of some serum proteins. The growth rates and maximum population density are comparable to those achieved using the expensive foetal calf serum.

EXAMPLE 3

The growth rate of human lymphoblasts cells in culture is comparable when the medium contains foetal calf serum and the cheaper swine serum. In both these cases the growth of the cells is better than that attained by using lamb serum.

MICH strain human lymphoblasts cells age grown in shake flask cultures in conventional media to which are added 10% foetal calf serum, swine, lamb, chicken, newborn calf or horse serum, each of these sera being commerical preparations. The minimum population doubling time and maximum population density are shown in the table below. Growth is on the medium containing foetal calf serum.

TABLE 2

| Serum (10% v/v) | Minimum Population Doubling Time (h) | Maximum Population/ml $\times 10^5$ (inoculum dedected) |
|---|---|---|
| Foetal Calf | 19 – 26 | 10 – 13 |
| Swine | 16 – 25 | 11 – 13 |
| Lamb | 68 | 4 |
| Horse | 18 | 11 |
| Chickens | — | 0 |
| Newborn Calf | 34 | 7.7 |

(With horse serum there is batch to batch variation with cell lines other than MICH).

EXAMPLE 4

The effect of serum concentration on growth of $BR_17$ cells in RPM1 No. 1640 in a shake flask wherein the growth medium is supplemented with 1 mg/ml of methylcellulose is illustrated as follows:

| % v/v Serum in Culture | Maximum Population/ml $\times 10^5$ Swine Serum | Inoculum Deducted Foetal Calf Serum |
|---|---|---|
| 0.5 | 3.7 | 1 |
| 1.0 | 5.0 | 2.7 |
| 2.0 | 6.4 | 3.4 |
| 5.0 | 6.9 | 6.6 |
| 10.0 | 8.0 | 7.0 |

What is claimed is:

1. A culture medium for lymphoblast cells comprising an aqueous nutrient medium containing 0.5 – 20% swine serum and about 0.1% of a surfactant which inhibits the precipitation of protein.

2. A culture medium for lymphoblast cells comprising an aqueous nutrient medium containing 0.5 – 20% swine serum and about 0.05 – 5% methyl cellulose to inhibit protein precipitation.

3. In a method for culturing lymphoblast cells of the type involving culturing cells in an aqueous nutrient medium containing animal serum the improvement which comprises using swine serum in combination with a surfactant to inhibit the precipitation of serum protein.

4. In a method for culturing lymphoblast cells of the type involving culturing cells in an aqueous nutrient medium containing animal serum the improvement which comprises using 0.5 – 20% swine serum in combination with about 0.05 – 5% methyl cellulose.

5. A growth medium for culturing lymphoblast cells comprising an aqueous nutrient medium containing 0.5 – 20% swine serum and about 0.05 – 5% polyoxyethylene-polyoxypropylene copolymer to inhibit protein precipitation.

* * * * *